United States Patent [19]

Wells et al.

[11] Patent Number: 5,883,058
[45] Date of Patent: *Mar. 16, 1999

[54] HIGH LATHER STYLING SHAMPOOS

[75] Inventors: Robert Lee Wells, Cincinnati, Ohio; Jon Robert Behrens, Kobe, Japan

[73] Assignee: The Procter & Gamble Company, Cincinnati, Ohio

[ * ] Notice: The term of this patent shall not extend beyond the expiration date of Pat. No. 5,672,576.

[21] Appl. No.: 520,631

[22] Filed: Aug. 29, 1995

[51] Int. Cl.$^6$ ...................................................... C11O 1/83
[52] U.S. Cl. ........................ 510/127; 510/119; 510/123; 510/125; 424/70.11; 424/70.24
[58] Field of Search ..................................... 252/549, 550, 252/551, 557; 510/119, 123, 125, 127; 424/70.24, 70.11

[56] References Cited

U.S. PATENT DOCUMENTS

| | | | |
|---|---|---|---|
| 4,196,190 | 4/1980 | Gehman et al. | 424/47 |
| 4,272,511 | 6/1981 | Papantoniou et al. | 424/47 |
| 4,784,801 | 11/1988 | Hoeffkes et al. | 252/554 |
| 5,084,212 | 1/1992 | Farris et al. | 252/554 |
| 5,104,642 | 4/1992 | Wells et al. | 424/47 |
| 5,120,532 | 6/1992 | Wells et al. | 424/70 |
| 5,310,508 | 5/1994 | Subramanyam et al. | 252/549 |
| 5,391,368 | 2/1995 | Gerstein | 424/70.13 |
| 5,514,302 | 5/1996 | Brown | 252/545 |
| 5,580,494 | 12/1996 | Sandhu et al. | 510/125 |

FOREIGN PATENT DOCUMENTS 0323715  12/1989  European Pat. Off. .

*Primary Examiner*—Paul Lieberman
*Assistant Examiner*—Necholas Ogden
*Attorney, Agent, or Firm*—Joan B. Tucker; William J. Winter; Tara M. Rosnell

[57] ABSTRACT

The present invention relates to hair shampoo compositions which have improved cleansing, lathering, and styling benefits=. These shampoo compositions comprise an alkyl glyceryl ether sulfonate surfactant, a hair styling polymer, a non-polar volatile solvent, and water. These compositions are useful for cleansing the hair and for providing a hair styling benefit.

26 Claims, No Drawings

HIGH LATHER STYLING SHAMPOOS

TECHNICAL FIELD

The present invention relates to hair shampoo compositions which have improved cleansing, lathering, and styling benefits. These shampoo compositions comprise an alkyl glyceryl ether sulfonate surfactant, optionally in combination with one or more additional surfactants. These compositions also comprise a hair styling polymer which is incorporated in a non-polar volatile solvent, which are together dispersed in the shampoo composition. Preferred embodiments of the present invention additionally comprise a hair conditioning agent. These preferred embodiments provide hair cleansing, styling, and conditioning benefits from a single product.

BACKGROUND OF THE INVENTION

In washing, drying and styling one's hair, several end results are desired. Firstly, and most obviously, one desires that the hair be thoroughly cleansed. Most desirable is a hair care process which maintains the look and feel of clean hair between hair washings.

Also, one desires a hair care process or product that provides hair styling benefits, especially hair style achievement and hold. Such style retention is generally accomplished by either of two routes: permanent chemical alteration or temporary alteration of hair style and shape. A permanent alteration, for example a chemical perm, involves the use of chemical agents to react with the hair in order to achieve the desired effect. This permanent chemical alteration of the hair, however, is not an object of the present invention. The styling benefit provided by the present invention is a temporary alteration. A temporary alteration is one which can be removed by water or by shampooing. In other words, it is a non-permanent alteration.

Temporary style alteration has generally been accomplished by means of the application of a separate composition or compositions after the shampooing process to provide style achievement and hold of hair. The materials used to provide these temporary styling benefits have generally been resins or gums that are usually applied in the form of mousses, gels, lotions, or sprays. This approach presents several significant drawbacks to the user. It requires a separate step following shampooing to apply the styling composition. In addition, many of these styling agents are aesthetically unappealing, leaving the hair feeling sticky or stiff after application of the styling composition, thereby defeating the purpose of the cleansing process. Moreover, many styling agents do not provide a long-lasting style benefit or provide a styling benefit that is too easily disturbed.

While the shampoo compositions that are disclosed in the prior art provide cleansing and conditioning benefits, they do not provide effective styling benefits. The benefits derived from styling are highly desirable. However, styling agents, such as styling polymers, cannot be readily incorporated into conventional shampoos without suppressing the lathering and cleansing ability of the shampoos, or the ultimate deposition and performance of the styling polymer.

In the present invention, it has surprisingly been found that certain surfactant systems such as alkyl glyceryl ether sulfonates can provide high cleansing and lathering properties in a system also containing a styling polymer. Furthermore, it has been found that when the styling polymer is dissolved in a non-polar volatile solvent that the styling polymer is readily dispersed in the shampoo composition and that the polymer is deposited onto the hair during the cleansing and rinsing process. Previous developments in this area employed a styling polymer dissolved in a polar solvent, which was emulsified into a shampoo base. See U.S. Pat. No. 5,120,532, to Wells et al., issued Jun. 9, 1993, which is incorporated by reference herein in its entirety. Polar solvents, however, can inhibit the deposition of the styling polymer. These solvents tend to be too soluble in the shampoo base, and can carry the styling polymer into the water phase of the shampoo and away from the hair into the the rinse water during the rinsing process. In addition, many of the commonly used polar solvents have strong objectionable odors or may be hydrolytically unstable in an aqueous envoirnment. A non-polar solvent would be prefereable in such instances, however, non-polar solvents tend to interfere with the cleansing and lathering ability of the surfactant base of the shampoo. Typical high lathering surfactants such as alkyl sulfates can build lather in the presence of non-polar solvents, but have the disadvantage of reducing deposition so that no styling benefit is achieved. Alkyl glyceryl ether sulfonates are also known to be good lathering surfactants. See U.S. Pat. No. 2,979,465, to Parran et al., issued Apr. 11, 1961, which is incorporated by reference herein in its entirety. It has, however, surprisingly been found that alkyl glyceryl ether sulfonate surfactants are able to produce good cleansing and lathering without interfering with the deposition of a hair styling polymer dissolved in a non-polar volatile solvent.

The present invention relates to hair shampoo compositions which comprise an alkyl glyceryl ether sulfonate surfactant, a hair styling polymer, a non-polar volatile solvent for dissolving the polymer, and water. Shampooing with these products provides both hair cleansing and styling benefits from a single product. These compositions also have good lathering ability. It has also been discovered that when a hair conditioning agent is added to the aforementioned product, hair conditioning, cleansing, and styling benefits can be achieved from a single hair care product. It has also been discovered that the styling shampoo compositions of the present invention provide product viscosities that maintain product phase stability and a consumer pleasing aesthetic appearance.

It is therefore an object of the present invention to provide hair shampoo compositions which provide both effective hair cleansing and good styling properties from a single composition.

It is also an object of the present invention to provide hair shampoo compositions which provide good lathering ability.

It is also an object of the present invention to formulate hair shampoo compositions which provide good style retention benefits without leaving the hair with a stiff, sticky, or tacky feel.

It is also an object of the present invention to formulate hair shampoo compositions which also provide effective conditioning properties.

It is also an object of the present invention to provide an improved method for cleansing and styling the hair.

These and other objects will become readily apparent from the detailed description which follows.

SUMMARY OF THE INVENTION

The present invention relates to a lathering, hair styling shampoo composition comprising:

(a) from about 2% to about 25%, by weight, of an alkyl glyceryl ether sulfonate surfactant;

(b) from about 0.1% to about 10%, by weight, of a hair styling polymer;

(c) from about 0.1% to about 10%, by weight, of a non-polar volatile solvent for solubilizing said hair styling polymer, said non-polar volatile solvent having a boiling point of less than or equal to about 300° C., and a solubility in water at 25° C. of less than about 0.2% by weight; and (d) from about 50% to about 97.8% water;

wherein the weight ratio of said hair styling polymer to said non-polar volatile solvent is from about 10:90 to about 70:30.

The present invention also relates to methods for cleansing and styling the hair utilizing the compositions of the present invention. These methods comprise the steps of:

(i) wetting the hair with water, (ii) applying an effective amount of the shampoo composition to the hair, (iii) shampooing the hair with said composition, (iv) rinsing said composition from the hair, and (v) drying and styling the hair.

All percentages and ratios used herein are by weight of the total composition and all measurements made are at 25° C. or room temperature, unless otherwise designated. All weight percentages, unless otherwise indicated, are on an actives weight basis. The invention hereof can comprise, consist of, or consist essentially of, the essential as well as the optional ingredients and additional components described herein.

DETAILED DESCRIPTION OF THE INVENTION

The styling polymers and non-volatile solvents of the present invention can be used in a wide variety of hair styling products, including shampoos, hair sprays, hair lotions, hair tonics, hair mousses, and hair rinses.

The essential, as well as the optional, components of the present invention are described below.

Alkyl Glyceryl Ether Sulfonate Surfactant

The compositions of the present invention comprise an alkyl glyceryl ether sulfonate surfactant (also referred to herein as an "AGS" surfactant) as the cleansing and lathering ingredient. These compositions comprise from about 2% to about 25%, more preferably from about 3% to about 20%, and most preferably from about 4% to about 10% of the alkyl glyceryl ether sulfonate surfactant. These AGS surfactants are derived from an alkyl glyceryl ether containing a sulfonate or sulfonate salt group. These compounds generally can be described as an alkyl monoether of glycerol that also contains a sulfonate group.

These AGS surfactants can be described as generally conforming to the following structures:

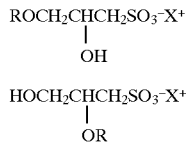

wherein R is a saturated or unsaturated straight chain, branched chain, or cyclic alkyl group having from about 10 to about 18 carbon atoms, preferably from about 11 to about 16 carbon atoms, and most preferably from about 12 to about 14 carbon atoms, and X is a cation selected from the group consisting of ammonium; mono-alkylsubstituted ammonium; di-alkylsubstituted ammonium; tri-alkylsubstituted ammonium; tetra-alkylsubstituted ammonium; alkali metal; alkaline metal; and mixtures thereof More preferably, the alkyl radicals, R in the above formulas, are saturated and straight chain.

The distribution of alkyl chain lengths in the AGS surfactant has some effect on the character of the overall shampoo product. A satisfactory distribution can be achieved in a commercially practicable way by using fatty alcohols derived from coconut oil and tallow. An equivalent distribution of alkyl chain lengths can be achieved using other starting materials. In the preparation of the coconut fatty alcohols used to provide the alkyl group of the AGS, preferably the middle cut of the coconut oil is taken. The higher boiling cut can be retained with the middle cut coconut oils if desired. In the preparation of the tallow fatty alcohols, a hydrogenation step is included to insure that they are substantially saturated.

The preferred AGS compounds are those where the alkyl group is derived from at least about 50% from alcohols of about 10 to about 18 carbons, having mainly monoglyceryl radicals present, with less than about 30% of diglyceryl radicals present. The AGS used in the Examples described below contains about 15% of diglyceryl ether sulfonates, and is preferred because of the ease of manufacturing this material. The term "AGS" is intended to include monoglyceryl, diglyceryl, and traces of the higher glyceryl compounds. Small amounts, that is less than about 3% total, of triglyceryl ether sulfonates and tetraglyceryl ether sulfonates can be present. Also included are AGS's derived from glyceryl ethers having branched or mixed branched and straight chain lengths that emulate the straight chain lengths.

The more preferred AGS surfactants for use in this invention are those which have a $C_{12-14}$ straight chain length, and are crystalline in structure. The preferred cation, "X", in the AGS surfactants is sodium. An example of a commercially available AGS surfactant useful herein includes sodium cocoglyceryl ether sulfonate, as listed in CTFA *International Cosmetic Ingredient Dictionary*, fifth edition, 1993, page 660, which is incorporated by reference herein in its entirety.

The AGS surfactants of this invention can be prepared using a variety of standard synthetic methods. The AGS surfactants can be preferably prepared by reacting fatty alcohols with a slight excess of epichlorohydrin, and then sulfonating the resulting chloroglyceryl ethers by means of the Streckerization Reaction. Secondary reaction products, such as alkyl diglyceryl ether disulfonates,

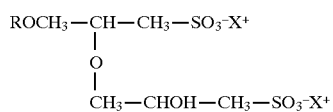

are formed in addition to the alkyl monoglyceryl ether sulfonate which is the primary product. Additional isomers of the diglyceryl compound are also formed and can be monosulfonated or disulfonated. For the purposes of this invention, the sodium alkyl glyceryl ether sulfonate should contain less than about 30% of the diglycerol ether product, and preferably less than about 25%. The balance is substantially monoglyceryl ether sulfonate. Generally, it is not desirable to reduce the alkyl diglyceryl ether content below about 5% for economic reasons.

The AGS surfactants useful in the present invention are more fully described in U.S. Pat. No. 2,979,465, to Parran et al., issued Apr. 11, 1961; U.S. Pat. No. 3,179,599, to Eaton et al., issued Apr. 20, 1965; British Patent No. 848,224, published Sep. 14, 1960; British Patent No. 791,415, published Mar. 5, 1958; U.S. Pat. No. 5,322,643, to Schwartz et al., issued Jun. 21, 1994; and U.S. Pat. No. 5,084,212, to Farris et al. issued Jan. 28, 1992; which are all hereby incorporated herein by reference in their entirety. These references also disclose various cleansing products in which the AGS surfactant of this invention can be used.

Hair Styling Polymer

The shampoo compositions of the present invention comprise a hair styling polymer. It is this component that provides the hair styling benefits to the user. The compositions of the present invention comprise from about 0.1% to about 10%, more preferably from about 0.3% to about 7%, and most preferably from about 0.5% to about 5% of the styling polymer.

A wide variety of hair styling polymers are known for use as styling agents. Many homopolymers, copolymers, and polymers combining three or more different monomer units are known in the art. Examples of such complex polymer systems are found in U.S. Pat. No. 5,120,531, to Wells et al., issued Jun. 9, 1992; U.S. Pat. No. 5,120,532, to Wells et al., issued Jun. 9, 1992; U.S. Pat. No. 5,104,642, to Wells et al., issued Apr. 14, 1992; U.S. Pat. No. 4,272,511, to Papantoniou et al., issued Jun. 9, 1981; and U.S. Pat. No. 4,196,190, to Gehman et al., issued Apr. 1, 1980, all of which are incorporated by reference herein in their entirety.

The polymers used herein are hydrophobic, water insoluble polymers. These polymers contain monomer units derived from polymerizable hydrophobic monomers. The term "hydrophobic monomer" means a monomer, that upon polymerization with like monomers, forms a water-insoluble homopolymer. The polymers can contain other monomer units which are not hydrophobic, however the polymer must remain water-insoluble as defined above.

The term "water-insoluble" polymer or homopolymer means a polymer that has a solubility in water at 25° C. of about 0.2% or less, calculated on a water plus polymer weight basis. "Solubility" for purposes hereof corresponds to the maximum concentration of polymer that can dissolve in water to form a solution that is substantially clear to the naked eye, as is well understood to those skilled in the art.

The hair styling polymer preferably has a glass transition temperature, Tg, i.e., the temperature at which the polymer changes from a brittle vitreous state to a plastic state, of at least about −20° C., preferably between about 0° C. and about 80° C., and most preferably between about 20° C. and about 60° C. Tg can be determined by differential scanning calorimetry, a method well known to one skilled in the art.

The hair styling polymers of the present invention have a weight average molecular weight of at least about 10,000. The molecular weight will generally be less than about 5,000,000, although higher molecular weights are not intended to be excluded. Preferably, the weight average molecular weight will be from about 30,000 to about 5,000,000, more preferably at least about 50,000, even more preferably at least about 75,000. The weight average molecular weight is preferably less than about 200,000, more preferably less than about 150,000. Weight average molecular weight, for purposes hereof, can be measured by methods known in the art suitable for determining the molecular weight of the sample to be analyzed, for example size exclusion chromatography utilizing column pore sizes of $10^3$, $10^5$, and $10^6$ angstroms, or other equivalent methods.

Suitable hydrophobic monomers include acrylic or methacrylic acid esters of $C_1$–$C_{18}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, and the like, the alcohols having from about 1–18 carbon atoms with the average number of carbon atoms being from about 4–12; vinyl acetate; vinyl chloride; vinylidene chloride; vinyl propionate; butadiene; cyclohexadiene; ethylene; propylene; vinyl toluene; and methoxy ethyl methacrylate. The polymers hereof can be homopolymers of such hydrophobic monomers or can be co-, ter-, and other higher polymers of hydrophobic monomers.

Preferred monomers include n-butyl methacrylate, isobutyl methacrylate, 2-ethylhexyl methacrylate, methyl methacrylate, t-butylacrylate, t-butylmethyacrylate, and mixtures thereof Especially preferred are t-butylacrylate, t-butylmethacrylate, and 2-ethylhexyl methacrylate.

The polymers hereof can be made by conventional polymerization techniques well known in the art including, for example, free radical polymerization.

Preferred examples of polymers useful in the present invention include the following: t-butyl acrylate/2-ethylhexyl acrylate copolymers having a weight/weight ratio of monomers of about 95/5, about 90/10, about 80/20, about 70/30, about 60/40, and about 50/50; t-butyl methacrylate/2-ethylhexyl acrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; t-butyl ethacrylate/2-ethylhexyl methacrylate copolymers having a weight/weight ratio of monomers of about 95/5, about 90/10, about 80/20, about 70/30, about 60/40, and about 50/50; and mixtures thereof.

Especially preferred polymers are t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; and mixtures thereof.

Non-Polar Volatile Solvent

The compositions of the present invention also comprise a non-polar volatile solvent or diluent for the styling polymer. The solvent is useful for diluting and solubilizing the polymer so that it can be dispersed as fluid particles in the shampoo composition. The amount of solvent to be used in the present shampoo compositions is an amount sufficient to solubilize the polymer and disperse it as a separate fluid phase in the shampoo composition. The compositions of the present invention comprise from about 0.10% to about 10%, preferably from about 0.5% to about 8%, and most preferably from about 1% to about 6% by weight of the polymer solvent. At levels below about 0.1% solvent, the polymer generally cannot be sufficiently diluted; while at levels above about 10% solvent, the shampoo's cleansing and lathering characteristics can be negatively affected. The weight/weight ratio of polymer to solvent in the present composition is from about 10:90 to about 70:30, preferably from about 30:70 to about 60:40.

Without being limited by theory, the solvent also aids in delivering style achievement by plasticising the polymer deposited on the hair, thereby making it more flexible and adhesive during the hair drying and styling process. Furthermore, the solvent should have a low solubility in water. Most preferred are the hydrocarbons which have a solubility in water of less than about 0.5% by weight, preferably less than 0.3% by weight, and most preferably less than 0.2% by weight. The particular polymer chosen for use in the present shampoo compositions must be soluble in the particular solvent utilized, thereby allowing the dispersion of the polymer and solvent mixture as a dispersed fluid phase in the shampoo composition.

Additionally, the solvents must not interact with the polymer styling agent in such a way that would substantially reduce the ability of the polymer to provide styling benefits to the hair under ordinary use situations. The solvents must, of course, be of sufficiently high purity and sufficiently low toxicity to render them suitable for administration to human hair.

The polymer solvent must also be volatile. Upon deposition of the polymer and solvent mixture onto the hair, the solvent is volatilized leaving only the styling polymer on the hair, thus providing the maximum styling benefits. Generally, the polymer solvents of the present invention have a boiling point of less than or equal to about 300° C., more preferably from about 90° C. to about 260° C., and most preferably from about 100° C. to about 200° C.

The volatile solvents useful in the present compositions can be hydrocarbons, ethers, or mixtures thereof. Most preferred are the hydrocarbons, especially the $C_{10}$–$C_{16}$ branched chain hydrocarbons. The most preferred solvents for use herein are isohexadecane, isododecane, 2,5-dimethyl decane, and mixtures thereof.

The hydrocarbons may be either straight or branched chain and may contain from about 8 to about 18 carbon atoms, preferably from about 10 to about 16 carbon atoms. Saturated hydrocarbons are preferred, although it is not necessarily intended to exclude unsaturated hydrocarbons. Examples of suitable straight chain hydrocarbons are decane, dodecane, decene, tridecene, and mixtures thereof Suitable branched chain hydrocarbons include isoparaffins of the above chain lengths. Isoparaffins are commercially available from Exxon Chemical Co. Examples include Isoparm™ and K ($C_{11}$–$C_{12}$ isoparaffins), and Isoparm™ L ($C_{11}$–$C_{13}$ isoparaffins). Other suitable branched chain hydrocarbons are isododecane and isohexadecane. These solvents are commercially available from Preperse, Inc. (South Plainfiled, N.J., USA) as Permethyl™ 99A and 101A, respectively. Useful ethers include di($C_5$–$C_7$) alkyl ethers and diethers, especially the di($C_5$–$C_6$) alkyl ethers such as isoamyl ether, dipentyl ether and dihexyl ether.

The most preferred volatile solvents hereof are the hydrocarbons.

Hair Styling Agent

The mixture of hair styling polymer and non-polar volatile solvent used in the present compositions is also referred to herein as the styling agent. The hair styling agent of the present invention comprises a mixture of a water-insoluble, hydrophobic hair styling polymer and a water-insoluble, non-polar volatile diluent.

The hair styling agent generally should have a hair styling polymer to volatile solvent weight ratio of from about 10:90 to about 70:30, preferably from about 20:80 to about 65:35, and more preferably from about 30:70 to about 60:40. The hair styling polymer is admixed with the non-polar volatile solvent, preferably in a weight ratio of from about 10:90 to about 70:30, more preferably from about 20:80 to about 65:35, and most preferably from about 30:70 to about 60:40. If the ratio of polymer to solvent is too low, the lathering performance of the shampoo composition is negatively affected. If the ratio of polymer to solvent is too high, the composition becomes too viscous and causes difficulty in the dispersion of the styling polymer. The hair styling agents should have an average particle diameter in the final shampoo product of from about 0.1 to about 100 microns, preferably from about 0.5 micron to about 25 microns. Particle size can be measured according to methods known in the art, including, for example optical microscopy.

Preferred examples of hair styling agents include the following materials. It should be noted that the numbers in parentheses following the polymers indicates the relative weight ratios of the monomers.

| | w/w ratio |
|---|---|
| Mixture A. | |
| Polymer: t-butyl acrylate/2-ethylhexyl methacrylate (90/10 w/w) | 40 |
| Solvent: isododecane | 60 |
| Mixture B. | |
| Polymer: t-butyl acrylate/2-ethylhexyl methacrylate (90/10 w/w) | 50 |
| Solvent: isododecane | 50 |
| Mixture C. | |
| Polymer: t-butyl methacrylate/2-ethylhexyl methacrylate (50/50 w/w) | 40 |
| Solvent: isohexadecane | 60 |
| Mixture D. | |
| Polymer: t-butyl methacrylate/2-ethylhexyl methacrylate (50/50 w/w) | 30 |
| Solvent: Isoparaffin Blend ($C_{11}$–$C_{12}$)[1] | 70 |
| Mixture E. | |
| Polymer: t-butyl acrylate/2-ethylhexyl methacrylate (60/40 w/w) | 40 |
| Isoparaffin Blend ($C_{11}$–$C_{13}$)[2] | 60 |

[1]Sold as Isopar H by Exxon, which is a mixture of $C_{11}$–$C_{12}$ isoparaffins.
[2]Sold as Isopar L by Exxon, which is a mixture of $C_{11}$–$C_{13}$ isoparaffins.

The compositions of the present invention comprise from about 50% to about 98.7%, more preferably from about 55% to about 85%, and most preferably from about 60% to about 75% of water.

ADDITIONAL COMPONENTS

Additional Surfactants

The compositions of the present invention can optionally comprise from about 0% to about 30%, preferably from about 2% to about 15%, and more preferably from about 4% to about 8% of a secondary surfactant selected from the group consisting of nonionic surfactants, anionic surfactants, cationic surfactants, amphoteric surfactants, zwitterionic surfactants, and mixtures thereof Such surfactants are well-known to those skilled in the art. Preferably, these surfactants are detersive surfactants. By "detersive" is meant that these surfactants provide a cleansing or detergent benefit.

Nonlimiting examples of suitable secondary surfactants for use in the compositions of the present invention are disclosed in McCutcheon's, *Detergents and Emulsifiers*, North American edition (1986), published by allured Publishing Corporation; McCutcheon's, *Functional Materials*, North American Edition (1992); U.S. Pat. No. 5,151,210, to Steuri et al., issued Sep. 29, 1992; U.S. Pat. No. 5,151,209, to McCall et al., issued Sep. 29, 1992; U.S. Pat. No. 5,120,532, to Wells et al., issued Jun. 9, 1992; U.S. Pat. No. 5,011,681, to Ciotti et al., issued Apr. 30, 1991; U.S. Pat. No. 4,788,006, to Bolich, Jr. et al., issued Nov. 29, 1988; U.S. Pat. No. 4,741,855, to Grote et al, issued May 3, 1988; U.S. Pat. No. 4,704,272, to Oh et al, issued Nov. 3, 1987; U.S. Pat. No. 4,557, 853, to Collins, issued Dec. 10, 1985; U.S. Pat. No. 4,421,769, to Dixon et al., issued Dec. 20, 1983; and U.S. Pat. No. 3,755,560, to Dickert et al., issued Aug. 28, 1973; each of these documents being incorporated herein by reference in its entirety.

The following are nonlimiting examples of surfactants useful herein. It should be recognized that care must be taken in determining the level of these surfactant materials used so as not to interfere with the deposition and performance characteristics of the styling polymer. Also, care must be taken to select the additional surfactant and its level, such that the mildness properties of the compositions are not compromised.

Among the nonionic surfactants that are useful herein are those that can be broadly defined as condensation products of long chain alcohols, e.g. C8–30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625CS from Henkel).

Other useful nonionic surfactants include the condensation products of alkylene oxides with fatty acids (i.e. alkylene oxide esters of fatty acids). When these particular nonionics are used, it is preferable to use them at low concentrations, preferably in combination with one or more of the other surfactants disclosed herein. These materials have the general formula $RCO(X)_nOH$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100. Other nonionic surfactants are the condensation products of alkylene oxides with 2 moles of fatty acids (i.e. alkylene oxide diesters of fatty acids). These materials have the general formula $RCO(X)_nOOCR$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100. Other nonionic surfactants are the condensation products of alkylene oxides with fatty alcohols (i.e. alkylene oxide ethers of fatty alcohols). These materials have the general formula $R(X)_nOR'$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100 and R' is H or a C10–30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are C10–30 alkyl groups, X is —OCH$_2$CH$_2$— (i.e. derived from ethylene glycol or oxide) or —OCH$_2$CHCH$_3$—(derived from propylene glycol or oxide), and n is an integer from about 1 to about 100. Nonlimiting examples of these alkylene oxide derived nonionic surfactants include ceteth-1, ceteth-2, ceteth-6, ceteth-10, ceteth-12, ceteareth-2, ceteareth-6, ceteareth-10, ceteareth-12, steareth-1, steareth-2, steareth-6, steareth-10, steareth-12, PEG-2 stearate, PEG-4 stearate, PEG-6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polyhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809, 060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

A wide variety of anionic surfactants are useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanolamine. Examples of these materials are sodium lauryl sulfate and ammonium lauryl sulfate.

Another suitable class of anionic surfactants are the water-soluble salts of the organic, sulfuric acid reaction products of the general formula:

$$R_1—SO_3—M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Cationic surfactants can also be utilized in the present invention. Nonlimiting examples of cationic surfactants useful herein include cationic ammonium salts such as those having the formula:

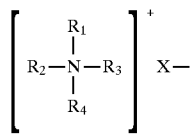

wherein $R_1$, is selected from an alkyl group having from about 12 to about 22 carbon atoms, or aromatic, aryl or alkaryl groups having from about 12 to about 22 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Other ammonium quaternary and amino surfactants include those in the form of ring structures formed by covalently linking of the radicals. Examples of such cationic surfactants include imidazolines, imidazoliniums, and pyridiniums, etc., wherein said surfactant has at least one nonionic hydrophile-containing radical as set forth above. Specific examples include 2-heptadecyl-4,5-dihydro-1H-imidazol-1-ethanol, 4,5-dihydro-1-(2-hydroxyethyl)-2-isoheptadecyl-1-phenylmethylimidazolium chloride, and 1-[2-oxo-2-[[2-[(1-oxooctadecyl)oxy]ethyl]amino]ethyl] pyridinium chloride.

Alternatively, other useful cationic surfactants include amino-amides, wherein in the above structure $R_1$ is alternatively $R_5CO—(CH_2)_n—$, wherein $R_5$ is an alkyl group having from about 12 to about 22 carbon atoms,' and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Other cationic surfactants for use in the present invention are those which are useful for providing conditioning benefits, particularly hair conditioning properties and which are quaternary ammonium or amino compounds having at least one N-radical containing one or more nonionic hydrophilic moieties selected from alkoxy, polyoxyalkylene, alkylamido, hydroxyalkyl, and alkylester moieties, and combinations thereof. The surfactant contains at least one hydrophilic moiety within 4 (inclusive), preferably within 3 (inclusive), carbon atoms of the quaternary nitrogen or cationic amino nitrogen. For purposes herein, this means that the closest non-carbon atom in the hydrophilic moiety to the cationic nitrogen must be within the stated number of carbon atoms relative to said nitrogen. Additionally, carbon atoms that are part of a hydrophilic moiety, e.g., carbon atoms in a hydrophilic polyoxyalkylene (e.g.,—$CH_2$—$CH_2$—O—), that are adjacent to other hydrophilic moieties are not counted as when determining the number of hydrophilic moieties within 4, or preferably 3, carbon atoms of the cationic nitrogen. In general, the alkyl portion of any hydrophilic moiety is preferably a $C_1$–$C_3$ alkyl. Suitable hydrophile-containing radicals include, for example, ethoxy, propoxy, polyoxyethylene, polyoxypropylene, ethylamido, propylamido, hydroxymethyl, hydroxyethyl, hydroxypropyl, methylester, ethylester, propylester, or mixtures thereof, as nonionic hydrophile moieties.

Specific examples of preferred quaternary ammonium salts include polyoxyethylene (2) stearyl methyl ammonium chloride, methyl bis (hydrogenated tallowamidoethyl) 2-hydroxyethyl ammonium methyl sulfate, polyoxypropylene (9) diethyl methyl ammonium chloride, tripolyoxyethylene (total PEG=10) stearyl ammonium phosphate, bis(N-hydroxyethyl -2-oleyl imidazolinium chloride) polyethylene glycol (12), and isododecylbenzyl triethanolammonium chloride.

Salts of primary, secondary and tertiary fatty amines are also preferred cationic surfactant materials. The alkyl groups of such amines preferably have from about 1 to about 30 carbon atoms and must contain at least one, preferably 2 to about 10, nonionic hydrophilic moieties selected from alkoxy, polyoxyalkylene, alkylamido, hydroxyalkyl, and alkylester moieties, and mixtures thereof. Secondary and tertiary amines are preferred, tertiary amines are particularly preferred. Specific examples of suitable amines include diethyl aminoethyl polyoxyethylene (5) laurate, coco polyglyceryl-4 hydroxypropyl dihydroxy ethylamine, and dihydroxyethyl tallowamine hydrochloride.

The cationic conditioning agents for use herein may also include a plurality of ammonium quaternary moieties or amino moieties, or a mixture thereof.

Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[CH_2)_m CO_2M]_2$ and $RNH(CH_2)_m CO_2M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine).

The above-mentioned surfactants can optionally be used in combination with AGS in the hair care compositions of the present invention. Preferred surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, cocoamidopropyl betaine, cocobetaine, lauryl amido propyl betaine, oleyl betaine, and cocoamphocarboxyglycinate.

The most preferred of the optional surfactants for use herein are ammonium laureth sulfate and cocoamidopropyl betaine.

Conditioning Agent

The shampoo compositions of the present invention also preferably comprise a hair conditioning agent. It is this agent that provides additional hair conditioning benefits such as ease of combing, soft hair feel, and manageability to the user. The resulting shampoo composition provides hair cleaning, styling and conditioning benefits in one product.

Cationic surfactants, as described above, can be used to give some conditioning benefits in the present compositions.

Similarly protein derivatives, such as hydrolyzed animal proteins, for example, Crotein SPA (Croda) or Lexeine X250 (Inolex) or Poly-peptide LSN (Stephan), can be used to provide conditioning benefits.

The hair conditioning agent of the present invention can be a non-volatile siloxane or a siloxane-containing material and is present at a level of from about 0.01% to about 10% of the shampoo composition, preferably from about 0.1% to about 5%, most preferably from about 0.2% to about 3%.

Siloxanes (see, for example, U.S. Pat. No. 3,208,911, Oppliger, issued Sep. 28, 1965) and siloxane-containing polymers have been taught for use in hair conditioning compositions. U.S. Pat. No. 4,601,902, Fridd et al., issued Jul. 22, 1986, describes hair conditioning or shampoo/conditioner compositions which include a polydiorganosiloxane having quaternary ammonium substituted groups attached to the silicon, and a polydiorganosiloxane having silicon-bonded substituents which are amino-substituted hydrocarbon groups. U.S. Pat. No. 4,654,161, Kollmeier et al., issued Mar. 31, 1987, describes a group of organopolysiloxanes containing betaine substituents. When used in hair care compositions, these compounds are said to provide good conditioning, compatibility with anionic components, hair substantivity, and low skin irritation. U.S. Pat. No. 4,563,347, Starch, issued Jan. 7, 1986, relates to hair conditioning compositions which include siloxane components containing substituents to provide attachment to hair. Japanese Published Application 56-129,300, Lion Corporation, published Oct. 9, 1981, relates to shampoo conditioner compositions which include an organopolysiloxane-oxyalkylene copolymer together with an acrylic resin. U.S. Pat. No. 4,479,893, Hirota et al., issued Oct. 30, 1984, describes shampoo conditioner compositions containing a phosphate ester surfactant and a silicon derivative (e.g., polyether- or alcohol-modified siloxanes). Polyether-modified polysiloxanes are also disclosed for use in shampoos in U.S. Pat. No. 3,957,970, Korkis, issued May 18, 1976. U.S. Pat. No. 4,185,087, Morlino, issued Jan. 22, 1980, describes quaternary nitrogen derivatives of trialkylamino hydroxy organosilicon compounds which are said to have superior hair conditioning properties. Each of the above mentioned documents in this paragraph are incorporated herein by reference in its entirety.

Siloxane-derived materials have also been used in hair styling compositions. Japanese Published Application 56-092,811, Lion Corporation, published December 27, 1979, describes hair setting compositions which comprise an amphoteric acrylic resin, a polyoxyalkylene-denatured organopolysiloxane, and polyethylene glycol. U.S. Pat. No. 4,744,978, Homan et al., issued May 17, 1988, describes hair styling compositions (such as hair sprays) which include the combination of a carboxyfunctional polydimethylsiloxane and a cationic organic polymer containing amine or ammonium groups. Hair styling compositions which include polydiorganosiloxanes and a cationic organic polymer are taught in U.S. Pat. No. 4,733,677, Gee et al., issued Mar. 29, 1988, and U.S. Pat. No. 4,724,851, Cornwall et al., issued Feb. 16, 1988. Finally, European Patent Application 117,360, Cantrell et al., published Sep. 5, 1984, discloses compositions, containing a siloxane polymer having at least one nitrogen-hydrogen bond, a surfactant, and a solubilized titanate, zirconate or germanate, which act as both a conditioner and a hair styling aid. Each of the above mentioned documents in this paragraph are incorporated herein by reference in its entirety.

Nonvolatile silicone fluids are useful as the conditioning agent component in the shampoo compositions of the present invention. Examples of such materials include polydimethylsiloxane gums, aminosilicones and phenylsilicones. More specifically, materials such as polyalkyl or polyaryl siloxanes with the following structure:

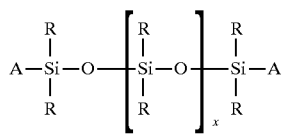

wherein R is alkyl or aryl, and x is an integer from about 7 to about 8,000 may be used. A represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on the hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

Suitable methods for preparing these silicone materials are disclosed in U.S. Pat. Nos. 2,826,551 and 3,964,500 and references cited therein, each of which are incorporated by reference in its entirety. Silicones useful in the present invention are also commercially available. Suitable examples include Viscasil, a trademark of the General Electric Company and silicones offered by Dow Corning Corporation and by SWS Silicones, a division of Stauffer Chemical Company.

Other useful silicone conditioning materials include materials of the formula:

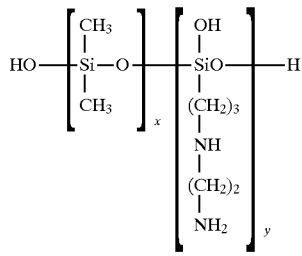

in which x and y are integers which depend on the molecular weight, the average molecular weight being approximately between 5,000 and 10,000. This polymer is also known as "amodimethicone".

Other silicone cationic polymer conditioning agents which can be used in the present compositions correspond to the formula:

in which G is chosen from the group consisting of hydrogen, phenyl, OH, $C^1$–$C^8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R^1$ is a monovalent radical of formula $C_qH^2_qL$ in which q is an integer from 2 to 8 and L is chosen from the groups

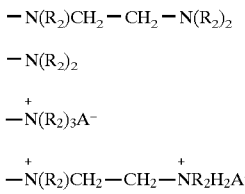

in which $R_2$ is chosen from the group consisting of hydrogen, phenyl, benzyl, a saturated hydrocarbon radical, preferably an alkyl radical containing from 1 to 20 carbon atoms, and A denotes a halide ion.

These compounds are described in greater detail in European Patent Application EP 95,238, which is incorporated by reference herein in its entirety. An especially preferred polymer corresponding to this formula is the polymer known as "trimethylsilylamodimethicone" of formula:

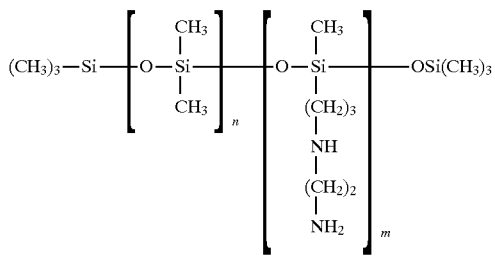

Other silicone cationic polymer conditioning agents which can be used in the present compositions correspond to the formula:

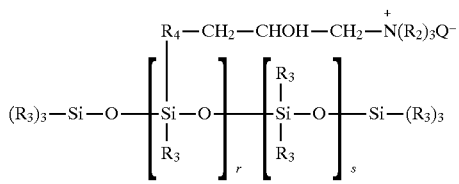

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably a $C_1$–$C_{18}$ alkylene radical or a $C_1$–$C_{18}$, and preferably $C_1$–$C_8$, alkyleneoxy radical;

Q is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017, which is incorporated by reference in its entirety. A polymer of this class which is especially preferred is that sold by UNION CARBIDE under the name "UCAR SILICONE ALE 56".

The compositions of the present invention can also comprise a water soluble, cationic hair conditioning agent. Although these cationic hair conditioning agents are not necessary for the styling benefit, they have been shown to aid deposition of the hair styling polymer and achievement of the styling benefit. The cationic hair conditioning agent hereof will generally be present at levels of from about 0.05% to about 5%, preferably from about 0.1% to about 4%, more preferably from about 0.2% to about 3%, by weight, of the shampoo composition. The water soluble cationic conditioning agents hereof can include organic cationic polymers, organic cationic surfactants, and cationic silicone fluids. By "water soluble", what is meant is a material which is soluble in water at a concentration of 0.1% in water (distilled or equivalent) at 25° C. Preferably, the water soluble cationic conditioning agent will be soluble at 0.5% concentration, more preferably at 1.0% concentration. In general, the polymer will be considered soluble if it forms a substantially clear solution to the naked eye.

The water-soluble cationic polymers useful in the hair conditioning agent hereof are polymers that can provide conditioning benefits to hair and that are soluble in the shampoo composition. Any cationic polymers which can provide these benefits can be used. As used herein, the term "polymer" shall include materials whether made by polymerization of one type of monomer or made by two (i.e., copolymers) or more types of monomers.

The cationic organic polymers hereof will generally have a weight average molecular weight which is at least about 5,000, typically at least about 10,000, and is less than about 10 million. Preferably, the molecular weight is from about 100,000 to about 2 million. The cationic polymers will have cationic nitrogen-containing moieties such as quaternary ammonium or cationic amino moieties, or a mixture thereof.

Those skilled in the art will recognize that the charge density of amino-containing polymers may vary depending upon pH and the isoelectric point of the amino groups. The polymer should be within the above solubility limits at the pH of intended use, which will in general be from about pH 3 to about pH 9, most generally from about pH 4 to about pH 8.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 5th edition, edited by Wenninger and McEwen, (The Cosmetic, Toiletry, and Fragrance Association, Inc., Washington, D.C., 1993).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are $C_1$–$C_7$ alkyls, preferably lower alkyls such as the $C_1$–$C_3$ alkyls, more preferably $C_1$ and $C_2$ alkyls.

The cationic polymers hereof can comprise mixtures of monomer units derived from amine- and/or quaternary ammonium-substituted monomer and/or compatible spacer monomers.

Suitable cationic hair conditioning polymers include, for example. copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

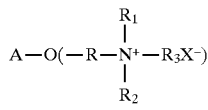

wherein: A is an anhydroglucose residual group, such as a starch or cellulose anhydroglucose residual, R is an alkylene oxyalkylene, polyoxyalkylene, or hydroxyalkylene group, or combination thereof, R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less, and X is an anionic counterion, as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their Jaguar R series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

As discussed above, the cationic polymer hereof is water soluble. This does not mean, however, that it must be soluble in the shampoo composition. Preferably however, the cationic polymer is either soluble in the shampoo composition, or in a coacervate phase in the shampoo composition formed by the cationic polymer and anionic material. Coacervates of the cationic polymer can be formed with anionic surfactants or with anionic polymers that can optionally be added to the compositions hereof (e.g., sodium polystyrene sulfonate).

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature. Coacervate systems and the effect of these parameters has previously been studied. See, for example, J. Caelles, et al., "Anionic and Cationic Compounds in Mixed Systems", Cosmetics & Toiletries, Vol. 106, April 1991, pp 49–54, C. J. van Oss, "Coacervation, Complex-Coacervation and Flocculation", J. Dispersion Science and Technology, Vol. 9 (5,6), 1988–89, pp 561–573, and D. J. Burgess, "Practical Analysis of Complex Coacervate Systems", J. of Colloid and Interface Science, Vol. 140, No. 1, November 1990, pp 227–238.

It is believed to be particularly advantageous for the cationic polymer to be present in the shampoo in a coacervate phase, or to form a coacervate phase upon application or rinsing of the shampoo to or from the hair. Coacervates are believed to more readily deposit on the hair. Thus, in general, it is preferred that the cationic polymer exist in the shampoo as a coacervate phase or form a coacervate phase upon dilution. If not already a coacervate in the shampoo, the cationic polymer will preferably exist in a coacervate form in the shampoo upon dilution with water to a water-:shampoo composition weight ratio of about 20:1, more preferably at about 10:1, even more preferably at about 8:1.

Techniques for analysis of formation of coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

Conditioning ingredients such as oils and emollients can also be incorporated into the styling shampoo compositions of this invention.

Other Optional Ingredients

The high lather styling shampoo compositions herein can contain a variety of other optional components suitable for rendering such compositions more cosmetically or aesthetically acceptable or to provide them with additional usage benefits. Such conventional optional ingredients are well-known to those skilled in the art, e.g., pearlescent aids, such as coated mica, ethylene glycol distearate, and PEG 3 distearate; opacifiers such as $TiO_2$; preservatives, such as benzyl alcohol, Glydant, Kathon, methyl paraben, propyl paraben and imidazolidinyl urea; fatty alcohols, such as cetearyl alcohol; sodium chloride; sodium sulfate; polyvinyl alcohol; ethyl alcohol; pH adjusting agents, such as citric acid, sodium citrate, succinic acid, phosphoric acid, monosodium phosphate, disodium phosphate, sodium hydroxide, and sodium carbonate; coloring agents, such as any of the FD&C or D&C dyes; perfumes; sequestering agents, such as disodium ethylenediamine tetra-acetate; and polymer plasticizing agents, such as glycerin and propylene glycol. The present compositions can also optionally comprise thickeners and viscosity modifiers, such as a diethanolamide of a long chain fatty acid (e.g., PEG 3 lauric diethanolamide), lauramide DEA, cocomonoethanol amide, guar gum, xanthan gum, Crothix (PEG 150 Pentaerythrityl Tetrastearate), methyl cellulose, hydroxyethyl cellulose, starches and starch derivatives. Various salts and electrolytes, preferably sodium chloride, can also be used as needed to adjust the viscosity of the present compositions. The compositions can comprise a nonionic long chain alkylated cellulose ether thickener such as those materials described in U.S. Pat. No. 4,228,277, Landoll, issued Oct. 14, 1980, which is incorporated herein by reference in its entirety.

Such optional ingredients generally are used individually at levels of from about 0.01% to about 10.0%, preferably from about 0.05% to about 5.0%, of the shampoo composition.

As with all compositions, the present invention should not contain optional components which unduly interfere with the cleaning and hair style holding performance of the present shampoo compositions.

Method of Making

The styling shampoo compositions of the present invention can be made using conventional formulation and mixing techniques. The hair styling polymer should first be dissolved in the non-polar volatile solvent. The remaining ingredients are combined in a separate vessel and the polymer and solvent mixture is added to these remaining ingredients. The composition should have a final viscosity of from about 1500 to about 12,000 cps. The viscosity of the composition can be adjusted using sodium chloride as needed.

Method of Use

The high lather styling shampoo compositions of the present invention are used in conventional ways to provide cleansing and styling hold benefits. Such methods generally involve application of an effective amount of the shampoo product to the wet hair, which is massaged through and then rinsed from the hair. By "effective amount" is meant an amount sufficient to provide the hair cleaning and styling hold benefits desired considering the length and texture of the hair. After the hair is shampooed with the compositions of the present invention, the hair is dried and styled in the usual ways of the user, e.g. combing, brushing, blow drying, curling, heat drying, etc.

EXAMPLES

The following examples illustrate the present invention. It will be appreciated that other modifications of the present invention within the skill of those in the cosmetic composition formulation art can be undertaken without departing from the spirit and scope of this invention.

Ingredients are identified by chemical or CTFA name.

All parts, percentages, and ratios herein are by weight unless otherwise specified.

Examples A–E

The following table defines the hair styling agents of the present invention. These hair styling agents are mixtures of hair styling polymers and non-polar volatile solvents which are used in Examples I–IX. All ratios herein are given on a weight/weight basis. It should be noted that the numbers in parentheses following the polymers indicates the relative weight ratios of the monomers.

|  | w/w ratio |
| --- | --- |
| Mixture A. | |
| Polymer: t-butyl acrylate/2-ethylhexyl methacrylate (90/10 w/w) | 40 |
| Solvent: isododecane | 60 |
| Mixture B. | |
| Polymer: t-butyl acrylate/2-ethylhexyl methacrylate (90/10 w/w) | 50 |
| Solvent: isododecane | 50 |
| Mixture C. | |
| Polymer: t-butyl methacrylate/2-ethylhexyl methacrylate (50/50 w/w) | 40 |
| Solvent: isohexadecane | 60 |
| Mixture D. | |
| Polymer: t-butyl methacrylate/2-ethylhexyl methacrylate (50/50 w/w) | 30 |
| Solvent: Isoparaffin Blend $(C_{11}-C_{12})^1$ | 70 |
| Mixture E. | |
| Polymer: t-butyl acrylate/2-ethylhexyl methacrylate (60/40 w/w) | 40 |
| Solvent: Isoparaffin Blend $(C_{11}-C_{13})^2$ | 60 |

[1]Sold as Isopar H by Exxon, which is a mixture of $C_{11}-C_{12}$ isoparaffins.
[2]Sold as Isopar L by Exxon, which is a mixture of $C_{11}-C_{13}$ isoparaffins.

The hair styling polymer and non-polar volatile solvent mixture is prepared by placing the appropriate hair styling polymer into a suitable vessel, and adding the appropriate non-polar volatile solvent to the vessel. The mixture is then stirred while heating to about 1600°–1800° F. until the polymer is completely dissolved.

Examples I–V

The following hair shampoo compositions are representative of the present invention.

|  | Weight % | | | | |
| --- | --- | --- | --- | --- | --- |
| Component | I | II | III | IV | V |
| Ammonium Laureth Sulfate | 2.00 | 2.00 | 2.00 | 8.00 | 2.00 |
| Cocoamidopropyl Betaine F | 6.00 | 6.00 | 6.00 | 6.00 | 6.00 |
| Ammonium Lauryl Sulfate | 0.00 | 2.00 | 0.00 | 0.00 | 0.00 |
| Alkyl Glycerol Sulfonate | 10.00 | 8.00 | 10.00 | 4.00 | 10.00 |
| Mixture A | 6.00 | — | — | — | — |
| Mixture B | — | 8.00 | — | — | — |
| Mixture C | — | — | 4.00 | — | — |
| Mixture D | — | — | — | 4.00 | — |
| Mixture E | — | — | — | — | 8.00 |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.00 | 2.00 | 2.00 | 2.00 | 2.00 |
| Cocomonoethanol amide | 0.70 | 0.70 | 0.70 | 0.70 | 0.70 |
| Fragrance | 0.8 | 0.8 | 0.8 | 0.8 | 0.8 |
| PEG-150 Pentaerythrityl Tetrastearate | 0.40 | 0.45 | 0.15 | 0.30 | 0.45 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| Polyquaternium 10 | 0.30 | 0.50 | 0.40 | 0.30 | 0.50 |
| Dimethicone[1] | 0.00 | 0.00 | 0.00 | 1.50 | 1.50 |
| DMDM Hydantoin | 0.37 | 0.37 | 0.37 | 0.37 | 0.37 |
| Water | QS 100 | QS 100 | QS 100 | QS 100 | QS 100 |

[1]This material is a 40/60 weight ratio blend of polydimethylsiloxane gum (GE SE 76, available from General Electric Company, Silicone Products Division, Waterford, NY, USA) and polydimethylsiloxane fluid (about 350 centistokes).

In a suitable vessel, the glycol distearate, cocomonoethanol amide, PEG-150 pentaerythrityl tetrastearate, cetyl alcohol, stearyl alcohol, monosodium phosphate, and disodium phosphate are combined with all of the AGS and half of each of the remaining surfactants [ammonium laureth sulfate, cocoamidopropyl Betaine F, (and ammonium lauryl sulfate when present)]. The mixture is then heated to about 160°–180° F. and stirred until the solids are melted. This mixture is cooled to room temperature. In another vessel, the polyquaternium-10 is predissolved in the water, then added to the other cooled ingredients with mixing. The appropriate polymer mixture and the remaining ingredients are added with stirring. The resulting shampoo product is useful for both cleansing the hair and for providing hair style holding benefits.

Example VI

The following hair shampoo composition is representative of the present invention.

| Component | Weight % |
| --- | --- |
| Alkyl Glycerol Sulfonate | 14.00 |
| Mixture A | 6.00 |
| Monosodium Phosphate | 0.1 |
| Disodium Phosphate | 0.2 |
| Glycol Distearate | 2.00 |
| Cocomonoethanol amide | 0.70 |
| Fragrance | 0.8 |
| PEG-150 Pentaerythrityl Tetrastearate | 0.40 |
| Cetyl Alcohol | 0.42 |
| Stearyl Alcohol | 0.18 |
| Polyquaternium 10 | 0.30 |
| DMDM Hydantoin | 0.37 |
| Water | QS |

This products is prepared using the method described in Examples I–V.

This shampoo product is useful for both cleansing the hair and for providing hair style holding benefits.

Examples VII–IX

The following are hair shampoo compositions which are representative of the present invention.

|  | Weight % | | |
| --- | --- | --- | --- |
| Component | VII | VIII | IX |
| Ammonium Laureth Sulfate | 2.00 | 2.00 | 2.00 |
| Cocoamidopropyl Betaine F | 6.00 | 6.00 | 6.00 |
| Ammonium Lauryl Sulfate | 0.00 | 0.00 | 0.00 |
| Alkyl Glycerol Sulfonate | 10.00 | 10.00 | 10.00 |
| Mixture A | 9.00 | 3.0 | 1.50 |
| Monosodium Phosphate | 0.1 | 0.1 | 0.1 |
| Disodium Phosphate | 0.2 | 0.2 | 0.2 |
| Glycol Distearate | 2.00 | 2.00 | 2.00 |
| Cocomonoethanol amide | 0.70 | 0.70 | 0.70 |
| Fragrance | 0.8 | 0.8 | 0.8 |
| PEG-150 Pentaerythrityl Tetrastearate | 0.50 | 0.15 | — |
| Cetyl Alcohol | 0.42 | 0.42 | 0.42 |
| Stearyl Alcohol | 0.18 | 0.18 | 0.18 |
| Polyquaternium 10 | 0.50 | 0.30 | 0.30 |
| Dimethicone[1] | 0.00 | 0.00 | 0.00 |
| DMDM Hydantoin | 0.37 | 0.37 | 0.37 |
| Water | QS 100 | QS 100 | QS 100 |

[1]This material is a 40/60 weight ratio blend of polydimethylsiloxane gum (GE SE 76, available from General Electric Company, Silicone Products Division, Waterford, NY, USA) and polydimethylsiloxane fluid (about 350 centistokes).

These products are prepared using the method described in Examples I–V.

These shampoo products are useful for both cleansing the hair and for providing hair style holding benefits.

What is claimed is:

1. A lathering, hair styling shampoo composition comprising:

(a) from about 2% to about 25%, by weight, of an alkyl glyceryl ether sulfonate surfactant;

(b) from about 0.1% to about 10%, by weight, of a hydrophobic, water-insoluble hair styling polymer having a Tg of from about −20° C. to about 80° C.;

(c) from about 0.1% to about 10%, by weight, of a non-polar volatile solvent for solubilizing said hair styling polymer, said non-polar volatile solvent is selected from the group consisting of hydrocarbons, ethers, and mixtures thereof; and having a boiling point of less than or equal to about 300° C., and a solubility in water at 25° C. of less than about 0.2% by weight; and (d) from about 50% to about 97.8% water; wherein the weight ratio of said hair styling polymer to said non-polar volatile solvent is from about 10:90 to about 70:30.

2. The shampoo composition of claim 1 wherein the ratio of said hair styling polymer to said non-polar volatile solvent is from about 30:70 to about 60:40.

3. The shampoo composition of claim 2 wherein said non-polar volatile solvent has a boiling point from about 90° C. to about 260° C.

4. The shampoo composition of claim 3 comprising from about 0.5% to about 5% of said non-polar volatile solvent.

5. The shampoo composition of claim 1 wherein said non-polar volatile solvent is a hydrocarbon.

6. The shampoo composition of claim 5 wherein said hydrocarbon is a straight or branched chain hydrocarbon having from about 8 to about 18 carbon atoms.

7. The shampoo composition of claim 6 wherein said hydrocarbon is selected from the group consisting of dodecane, isododecane, isotetradecane, isohexadecane, 2,5-dimethyldecane, and mixtures thereof.

8. The shampoo composition of claim 7 wherein said hydrocarbon is selected from the group consisting of isododecane, isohexadecane, and mixtures thereof.

9. The shampoo composition of claim 8 wherein said hydrocarbon is isododecane.

10. The shampoo composition of claim 1 wherein said non-polar volatile solvent is an ether.

11. The shampoo composition of claim 10 wherein said ether is selected from the group consisting of isoamyl ether, dipentyl ether, dihexyl ether, and mixtures thereof.

12. The shampoo composition of claim 1 wherein the alkyl glyceryl ether sulfonate surfactant comprises alkyl chains derived from at least about 50% from alcohols of about 10 to about 18 carbons, and contains less than about 30% diglycerol radicals.

13. The shampoo composition of claim 1 wherein the hair styling polymer comprises hydrophobic monomer units which are selected from the group consisting of n-butyl methacryl ate, isobutyl methacrylate, 2-ethylhexyl methacryl ate, methyl methacrylate, t-butyl acrylate, t-butyl methacrylate, and mixtures thereof.

14. The shampoo composition of claim 13 wherein the hair styling polymer comprises from about 0.5% to about 5% of said composition.

15. The shampoo composition of claim 14 wherein the hair styling polymer is selected from the group consisting of t-butyl acrylate/2-ethylhexyl methacrylate, t-butyl methacrylate/2-ethylhexyl methacrylate, and mixtures thereof.

16. The shampoo composition of claim 1 which further comprises from about 2% to about 15% by weight of a secondary surfactant selected from the group consisting of nonionic surfactants, anionic surfactants, cationic surfactants, amphoteric surfactants, zwitterionic surfactants, and mixtures thereof.

17. The shampoo composition of claim 16 wherein said secondary surfactant is an amphoteric surfactant.

18. The shampoo composition of claim 17 wherein said secondary surfactant is a betaine.

19. The shampoo composition of claim 18 wherein said betaine surfactant is cocoamidopropyl betaine.

20. The shampoo composition of claim 19 wherein said secondary surfactant is an anionic surfactant.

21. The shampoo composition of claim 20 wherein said secondary anionic surfactant is ammonium laureth sulfate.

22. The shampoo composition of claim 1 which further comprises a conditioning agent.

23. The shampoo composition of claim 22 wherein said conditioning agent is a cationic polymer.

24. The shampoo composition of claim 23 wherein said cationic polymer is a cationic cellulose.

25. The shampoo composition of claim 24 wherein said cationic cellulose is present at a level of from about 0.05% to about 1.0% by weight.

26. A method for cleansing and styling the hair comprising the steps of:
 (i) wetting the hair with water,
 (ii) applying an effective amount of the composition of claim 1 to the hair,
 (iii) shampooing the hair with said composition,
 (iv) rinsing said composition from the hair, and
 (v) drying and styling the hair.

* * * * *